United States Patent [19]

Eyre

[11] Patent Number: 5,688,652

[45] Date of Patent: *Nov. 18, 1997

[54] DETECTION OF COLLAGEN DEGRADATION IN VIVO

[75] Inventor: David R. Eyre, Mercer Island, Wash.

[73] Assignee: Washington Research Foundation, Seattle, Wash.

[*] Notice: The term of this patent shall not extend beyond the expiration date of Pat. Nos. 5,576,189, 5,300,434, 5,320,970, 5,473,052 and 5,472,884.

[21] Appl. No.: 561,842

[22] Filed: Nov. 22, 1995

Related U.S. Application Data

[63] Continuation of Ser. No. 229,569, Apr. 19, 1994, Pat. No. 5,472,884, which is a continuation of Ser. No. 708,529, May 31, 1991, Pat. No. 5,320,970, which is a continuation-in-part of Ser. No. 614,719, Nov. 21, 1990, Pat. No. 5,300,434, which is a continuation-in-part of Ser. No. 448,881, Dec. 1, 1989, Pat. No. 5,140,103, which is a continuation-in-part of Ser. No. 118,234, Nov. 6, 1987, Pat. No. 4,973,666.

[51] Int. Cl.$^6$ .................................................... G01N 33/53
[52] U.S. Cl. ..................... 435/7.1; 435/7.9; 435/975; 436/501; 436/512; 436/547; 436/808; 436/811; 530/387.1; 530/387.9; 530/388.9; 530/388.1; 530/389.1; 530/389.9; 530/391.1; 530/391.3
[58] Field of Search ................. 435/7.1, 7.7, 7.9, 435/975, 172.2, 70.21, 240.27; 436/501, 503, 504, 512, 547, 548, 86, 804, 808, 811, 822; 530/387.9, 387.1, 388.1, 388.9, 389.1, 389.2, 389.8, 391.1, 391.3

[56] References Cited

U.S. PATENT DOCUMENTS

| | | | |
|---|---|---|---|
| 3,600,132 | 8/1971 | Goverde | 436/90 |
| 4,094,646 | 6/1978 | Stern et al. | 436/20 |
| 4,298,593 | 11/1981 | Ling . | |
| 4,312,853 | 1/1982 | Timpl | 436/540 |
| 4,371,374 | 2/1983 | Cerami et al. | 436/87 |
| 4,504,587 | 3/1985 | Timpl et al. | 436/538 |
| 4,731,326 | 3/1988 | Thompson et al. . | |
| 4,774,227 | 9/1988 | Piez et al. . | |
| 4,973,666 | 11/1990 | Eyre | 530/323 |
| 5,140,103 | 8/1992 | Eyre . | |
| 5,300,434 | 4/1994 | Eyre | 435/240.2 |
| 5,320,970 | 6/1994 | Eyre | 436/536 |
| 5,455,179 | 10/1995 | Eyre . | |
| 5,472,884 | 12/1995 | Eyre | 436/518 |
| 5,473,052 | 12/1995 | Eyre | 530/387.9 |
| 5,532,169 | 7/1996 | Eyre . | |
| 5,576,189 | 11/1996 | Eyre . | |
| 5,607,862 | 3/1997 | Eyre . | |

FOREIGN PATENT DOCUMENTS

| | | |
|---|---|---|
| 128 041 | 6/1983 | European Pat. Off. . |
| 289 314 | 4/1988 | European Pat. Off. . |
| 0 505 210 A2 | 9/1992 | European Pat. Off. . |
| 0 424 428 B1 | 9/1994 | European Pat. Off. . |
| 394 296 | 1/1995 | European Pat. Off. . |
| 502 928 | 1/1996 | European Pat. Off. . |
| 2205643(13) | 5/1987 | United Kingdom . |
| WO 88/08980 | 11/1988 | WIPO . |
| WO 89/04491 | 5/1989 | WIPO . |
| WO 89/12824 | 12/1989 | WIPO . |
| WO 90/04417 | 5/1990 | WIPO . |
| WO 90/08195 | 7/1990 | WIPO . |
| WO 91/08478 | 6/1991 | WIPO . |
| WO 92/21698 | 12/1992 | WIPO . |

OTHER PUBLICATIONS

Black, D., Duncan, a. and Robins, S.P., "Quantitative analysis of the Pyridinium Crosslinks of Collagen in Urine Using Ion–Paired Reversed–Phase High–Performance Liquid Chromatography," *Analytical Biochemistry* 169:197–203 (1988).

Hartmann, et al., "Radioimmunoassay of Type I Collagen That Mainly Detects Degradation Products in Serum: Application to Patients with Liver Diseases," *Clin. Chem.*, 36(3):421–426 (1990).

Fujimoto and Moriguchi, "Pyridinoline, a non–reducible crosslink of collagen," *J. Biochem.*, 83:863–867, 1978.

Macek and Adam, Z. *Rheumatol.*, "Determination of collagen degradation products in human urine in osteoarthrosis," 46:237–240, 1987.

Eyre, David R., and Glimcher, Melvin J., "Evidence for Intramolecular Crosslinks in Chicken Bone Collagen, Isolation of Peptides Containing Allysine Aldol," *Chemical Abstracts*, 78:81202c, 1973.

Kühn, Klaus, "Chemical Properties of Collagen," In: *Immunochemistry of the Extracellular Matrix*, vol. I, pp. 1–29, CRC Press, Inc., 1982.

Robins and Duncan, "Cross–linking of collagen," *Biochem. J.*, 215:175–182 (1983).

Robins, Simon P., and Duncan, Alexander, "Pyridinium crosslinks of bone collagen and their location in peptides isolated from rat femur," *Biochimica et Biophysica Acta*, vol. 914, pp. 233–239.

(List continued on next page.)

*Primary Examiner*—James C. Housel
*Assistant Examiner*—Susan C. Wolski
*Attorney, Agent, or Firm*—Christensen O'Connor Johnson & Kindness PLLC

[57] ABSTRACT

Methods of determining collagen degradation in vivo, by quantitating the concentration of a peptide in a body fluid, the peptide having the following structure:

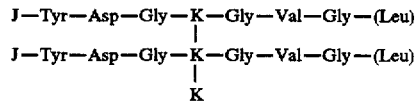

wherein

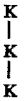

is hydroxylysyl pyridinoline or lysyl pyridinoline, and J is pyroglutamic acid or glutamine and (Leu) are optional leucines, are disclosed.

3 Claims, 1 Drawing Sheet

OTHER PUBLICATIONS

Henkel, Werner, Glanville, Robert W., and Oreifendorf, Dieter, "Characterisation of a type–I collagen trimeric cross–linked peptide from calf aorta and its cross–linked structure," *Eur. J. Biochem*, 165:427–436, 1987.

Hanson, et al., "A specific immunoassay for monitoring human bone resorption: quantitation of type I collagen cross–linked N–telopeptide in urine," *Journal of Bone and Mineral Research*, 7:1251–1256 (1992).

Del Pozo, A.M., et al., "Binding of 1–Anilinonsphthalene–8–Sulfonic Acid to Type I Collagen," *Int. J. Peptide Protein Res.*, 28:329–358, 1983.

Robins, "Analysis of the Crosslinking Components in Collagen and Elastin," *Methods of Biochemical Analysis*, vol. 28, pp. 329–379, John Wiley & Sons, 1982.

Fujimoto, Daisaburo, "Isolation and Characterization of a Fluorescent Material in Bovine Achilles Tendon Collagen," *Biochemical and Biophysical Research Communications*, vol. 76, pp. 1124–1129, 1977.

Seibel, et al., "Urinary Hydroxy–pyridinium Crosslinks Provide Indices of Cartilage and Bone Involvement in Arthritic Disease," *The Journal of Rheumatology*, 16(7):964–970 (1989).

Click and Bornstein, Isolation and Characterization of the Cyanogen Bromide Peptides from the α1 and α2 Chains of Human Skin Collagen, *Biochemistry* 9(24):4699–4706 (1970).

Krüger–Franke, M., et al., "Pyridinolinhaltige Kollagenbruchstücke im Urin bei Coxarthrose," *Z. Rheumatol.* 50:323–327 (1991).

Dickson et al., Analysis of the promoter region and the N–propeptide domain of the human proα2(I) collagen gene, *Nucleic Acids Research* 13(10):3427–3438 (1985).

Abbiati et al., Monitoring of free and total urinary pyridinoline and deoxypyridinoline in healthy volunteers: sample relationships between 24–h and fasting early morning urine concentrations, *Bone and Mineral*, 21:9–19 (1993).

Fujimori, Eiji, "Ultraviolet light– and ozone–induced changes in pyridinoline, a trisubstituted 3–hydroxypyridinium crosslink of collagen," *Biochimica et Biophysica Acta*, 828:104–106, 1985.

Sakura, Sachiko, and Fujimoto, Daisaburo, "Photolysis of pyridinoline, a cross–linking amino acid of collagen, by ultraviolet light," *Can. J. Biochem.*, 60:525–529, 1982.

Sakura, Sachiko, and Fujimoto, Daisaburo, "Electrochemical Behaviour of Pyridinoline, a Crosslinking Amino Acid of Collagen," *J. Biochem.*, 89:1541–1546, 1981.

Koob, T.J., Eyre, D.R., and Van Ness, K.P. "Detection and Photolysis of Hydroxypyridinium Cross–links in Cartilage Collagen in situ," *Orthopaedic Transactions*, VII: 251–252 (1983).

Rosmalen, F.M.A., Martens, M.F.W.C., van Hoek, M.J.C., et al., "Light Sensitivity of Deoxypyridinoline: Implications for the Collection of Urine," *J. Bone Miner. Res.* 9:B421 (1994).

Baurain, R., Larochelle, J., and Lamy, F. "Photolysis of Desmosine and Isodesmosine by Ultraviolet Light," *Eur. J. Biochem.* 67:155–164, 1976.

Blumsohn, A., Colwell, A., Naylor, K.E., et al., "Effect of Light and gamma–Irradiation on Pyridinoline and Telopeptides of Type I Collagen in Urine," *Clin. Chem.* 41:1195–1197, 1995.

Furthmayr, H., et al., "Different Antigenic Determinants in the Polypeptide Chains of Human Collagen," *Febs Letters*, 12(6):341–344.

Becker, U., Timpl, R., and Kuhn, K. "Carboxyterminal Antigenic Determinants of Collagen from Calf Skin: Localization within Discrete Regions of the Nonhelical Sequences," *Eur. J. Biochem.* 28:221–231 1972.

Kuhn, K. "The Classical Collagens: Types I, II, and III," *In: Structure and Function of Collagen Types*, (1987).

Rauterberg, J. "The C–Terminal Non–Helical Portion of the Collagen Molecule," *Clin. Ortho. Rel. Res.* 97:196–212 1973.

Davril, M., Han, K., Guay, M., et al., "Photolysis of Crosslinked Peptides from Elastin of Porcine Aorta," *FEBS Lett.* 98:128–134 1979.

Otter, A., Scott, P.G., and Kotovych, G. "Type I Collagen a–1 Chain C–Telopeptide: Solution Structure Determined by 600–MHz Proton NMR Spectroscopy and Implications for Its Role in Collagen Fibrillogenesis," *Biochemistry*, 27:3560–3567 1988.

van Hoek, M.J.C., Martens, M.F.W.C., Walchli, R., et al., "A Novel Polyclonal Antibody Against Deoxy–Pyridinoline to be used in a Radioimmunoassay," (1994). 2nd Workshop on Biophosphonates, Apr. 14–16; Nichols Institute, Diagnostics B.V.

Fuller, F. and Boedtker, H. "Sequence Determination and Analysis of the 3' Region of Chicken Pro–α1(I) and Pro–a__ (I) Collagen Messenger Ribonucleic Acids Including the Carboxy–Terminal Propeptide Sequences," *Biochemistry*, 20:996–1006 1981.

Rosmalen, F.M.A., Martens, M.F.W.C., van Hoek. M.J.C., et al., "Light Sensitivity of Deoxypyridinoline: Implications for the Collection of Urine," (1994). 16th Annual Meeting of the American Society of Bone and Mineral Research, Sep. 9–13, Nichols Institute, Diagnostics, B.V.

Gunja–Smith & Boucek, "Desmosines in human urine," *Biochem. J.*, 193:915–918, 1981.

Tellerova et al., "Determination of larger urinary peptides in osteoarthrosis by high–performance liquid chromatography," *Scand J Rheumatology* 15:52–56 (1986).

Adam, M. and Deyl, Z., "Altered expression of collagen phenotype in osteoarthrosis," *Clinica Chimica Acta.*, 133:25–32 (1983).

Johnstone et al., Immunochemistry in Practice, Blackwell Scientific Publications, Oxford, U.K., 1987, pp. 48–65.

Black, et al., "Urinary excretion of the hydroxypyridinium cross links of collagen in patients with rheumatoid arthritis," *Annals of the Rheumatic Diseases*, 48:641–644 (1989).

Seibel, et al., "Urinary Hydroxy–pyridinium Crosslinks Provide Indices of Cartilage and Bone Involvement in Arthritic Diseases," *The Journal of Rheumatology*, 16:964–970 (1989).

Baldwin, et al., "Structure of cDNA clones coding for human type II procollagen: The a1(II) chain is more similar to the a1(I) chain than two other a chains of fibrillar collagens," *Biochemistry Journal*, 262:521–528 (1989).

Ala–Kokko, et al., "Structure of cDNA clones coding for the entire preproα1(III) chain of human type III procollagen: Differences in protein structure from type I procollagen and conservation of codon preferences," *Biochemistry Journal*, 260:509–516 (1989).

Seibel, "Komponenten der extrazllularen Gewebematrix als potentielle 'Marker' des Bindegewebs–, Knorpel– und Knochenmetabolismus bei Erkrankungen des Bewegungsapparates," *Zeitschrift fur Rheumatologie*, 48:6–18 (1989).

Dodge and Poole, "Immunohistochemical Detection and Immunochemical Analysis of Type II Collagen Degradation in Human Normal, Rheumatoid, and Osteoarthritic Articular Cartilages and in Explants of Bovine Articular Cartilage Cultured with Interleukin 1," Journal of Clinical Investigation, 83:647–661 (1989).

Niemela, "Radioimmunoassays for Type III Procollagen Amino–Terminal Peptides In Humans," Clinical Chemistry, 31:1301–1304 (1985).

Sangiorgi, et al., "Isolation and partial characterization of the entire human proa1(II) collagen gene," Nucleic Acids Research, 13:2207–2225 (1985).

Loidl, et al., "Molecular cloning and carboxyl–propeptide analysis of human type III procollagen," Nucleic Acids Research, 12:9383–9394 (1984).

Wu and Eyre, "Identification of Hydroxypyridinium Cross–Linking Sites in Type II Collagen of Bovine Articular Cartilage," Biochemistry, 23:1850–1857 (1984).

Pierard, et al., "Radioimmunoassay for the Amino–Terminal Sequences of Type III Procollagen in Human Body Fluids Measuring Fragmented Precursor Sequences," Analytical Biochemistry, 141:127–136 (1984).

Rohde, et al., "Radioimmunoassay for type III procollagen peptide and its application to human liver disease," European Journal of Clinical Investigation, 9:451–459 (1979).

Russell, R.G.G., et al., "Biochemical Markers of Bone Turnover in Paget's Disease," Metab. Bone Dis. & Rel. Res., 4 & 5:255–262 (1981).

Drinkwater, B.L., et al., "Bone Mineral Density After Resumption of Menses in Amenorrheic Athletes," JAMA, 256:380–382 (1986).

Drinkwater, B.L., et al., "Bone Mineral Content of Amenorrheic and Eumenorrheic Athletes," The New England Journal of Medicine, 331:5; 277–281 (1984).

Fujimoto, D., "Evidence for Natural Existence of Pyridinoline Crosslink in Collagen," Biochemical and Biophysical Research Communications, 93:948–953 (1980).

Yamauchi, M. et al., "A Comparative Study of the Distribution of the Stable Crosslink, Pyridinoline, in Bone Collagens from Normal, Osteoblastoma, and Vitamin D–Deficient Chicks," Biochemical and Biophysical Research Communications, 102:59–65 (1981).

Kuboki, Y., et al., "Location of the Intermolecular Crosslinks in Bovine Dentin Collagen, Solubilization with Trypsin and Isolation of Cross–Link Peptides Containing Dihydroxylysinonorleucine and Pyridinoline," Biochemical and Biophysical Research Communications, 102:119–126 (1981).

Gunja–Smith, Z. and Boucek, R.J., "Collagen cross–linking compounds in human urine," Biochemical Journal, 197:759–762 (1981).

Tsuchikura, O., et al., "Pyridinoline Fluorescence in Cyanogen Bromide Peptides of Collagen," Biochemical and Biophysical Research Communications, 102:1203–1208 (1981).

Tsuda, M., et al., "Pyridinoline is a Real Moiety of Collagen," Biochemical and Biophysical Research Communications, 104:1407–1412 (1982).

Robins, S.P., "An enzyme–linked immunoassay for the collagen cross–link pyridinoline," Biochemical Journal, 207:617–620 (1982).

Banes, A.J., et al., "Nonmineralized and Mineralized Compartments of Bone: The Role of Pyridinoline in Nonmineralized Collagen," Biochemical and Biophysical Research Communications, 113:975–981 (1983).

Fujimoto, D., et al., "Analysis of Pyridinoline, a Cross–Linking Compound of Collagen Fibers, in Human Urine," J. Biochem., 94:1133–1136 (1983).

Eyre, D.R., et al., "Cross–Linking in Collagen and Elastin," Ann. Rev. Biochem., 53:717–748 (1984).

Light, N. and Bailey, A.J., "Collagen crosslinks: Location of pyridinoline in type I collagen," FEBS 2409, 182:503–508 (1985).

Wu, J–J. and Eyre, D.R., "Fine Powdering Exposes the Mineral–Protected Collagen of Bone to Protease Digestion," Calcif. Tissue Int., 42:243–247 (1988).

Fujimoto, D., et al., "Pyridinoline, A Non–Reducible Crosslink of Collagen. Quantitative Determination, Distribution, and Isolation of a Crosslinked Peptide," Chemical Abstracts 89(11):148, (Sep. 11, 1978).

Black, D., et al., "Quantitative Analysis of the Pyridinium Crosslinks of Collagen in Urine Using Ion–Paired Reversed––Phase High–Performance Liquid Chromatography," Chemical Abstracts 108(21):354, (May 23, 1988).

Fujimoto, D., et al., "Analysis of Pyridinoline, A Cross–Linking Compound of Collagen Fibers, in Human Urine," Chemical Abstracts 99(19):446–447, (Nov. 7, 1983).

Macek, J., et al., "Determination of Collagen Degradation Products in Human Urine in Osteoarthrosis," Chemical Abstracts 108(3):299, (Jan. 18, 1988).

Eyre, D.R., et al., "Quantitation of Hydroxypyridinium Crosslinks in Collagen by High–Performance Liquid Chromatography," Analytical Biochemistry, 137:380–388 (1984).

Robins, S.R., et al., "Measurement of the cross linking compound, pyridinoline, in urine as an index of collagen degradation in joint disease," Annals of the Rheumatic Diseases, 45:969–973 (1986).

Bernard, M.P., et al., "Nucleotide Sequences of Complementary Deoxyribonucleic Acids for the Proa1 Chain of Human Type I Procollagen. Statistical Evaluation of Structures that are Conserved During Evolution," Biochemistry, 22:5213–5223 (1983).

Goldstein, D., et al., "Simultaneous Measurement of DOPA, DOPAC, and Catecholamines in Plasma by Liquid Chromatography with Electrochemical Detection," ESA Review, vol. II, No. 1, 2–11 (1986).

Chu, M–L., et al., "Human proa1(I) collagen gene structure reveals evolutionary conservation of a pattern of introns and exons," Nature 310(26):337–340 (1984).

Robins, S.P., et al., "Measurement of Hydroxypyridinium Crosslinks of Collagen as an Index of Bone Matrix Degradation," An Abstract of a Paper, Lake Garda, Italy (1987).

Kang A.H. and Gross, J., "Amino Acid Sequence of Cyanogen Bromide Peptides from the Amino–Terminal Region of Chick Skin Collagen," Biochemistry 9:796–804 (1970).

Highberger, J.H., et al., "The Amino Acid Sequence of Chick Skin Collagen a1–CB7," Biochemistry 14(13):2872–2881 (1975).

Fietzek, P.P. and Kuhn, K., "The Covalent Structure of Collagen: Amino Acid Sequence of the N–Terminal Region of a2–CB5 from Rat Skin Collagen," FEBS Letters 36(3):289–291 (1973).

Dixit, S.N., et al., "Covalent Structure of Collagen: Amino Acid Sequence of a2–CB5 of Chick Skin Collagen Containing the Animal Collagenase Cleavage Site," Biochemistry, 18:3416–3422 (1979).

Dakkak, et al., "Modifications de l'hydroxyprolinurie peptidique au cours de la maladie de Paget et des ostéomes," Ann. Biol. Clin. 37:195–200 (1979).

Teitsson, et al., "Urinary excretion of pyridinium metabolites in a patient with Paget's Disease: new markers for collagen break-down," Abstracts, Scottish Society for Experimental Medicine, May 13, 1988.

Eyre, et al., "Collagen cross-linking in human bone and articular cartilage: Age-related changes in the content of mature hydroxypyridinium residues," Biochem. J. 252:495–500 (1988).

Whittle, et al., "Biochemical investigation of possible lesions in human aorta that predispose to dissecting aneurysms: pyridinoline crosslinks," Cardiovascular Research 21:161–168 (1987).

Gunja-Smith, Z., "An Enzyme-Linked Immunosorbent Assay to Quantitate the Elastin Crosslink Desmosine in Tissue and Urine Samples," Analytical Biochemistry 147:258–264 (1985).

Schuppan, et al., "Radioimmunoassay for the Carboxy-terminal Cross-linking Domain of Type IV (Basement Membrane) Procollagen in Body Fluids," J. Clin. Invest. 78:241–248 (Jul. 1986).

Eyre, D., "Collagen Cross-Linking Amino Acids," In: Methods in Enzymology, vol. 144, pp. 115–139, Academic Press, Inc., 1987.

Eyre, et al., "Identification of urinary peptides derived from cross-linking sites in bone collagen in Paget's Disease," Journal of Bone and Mineral Research, 3, Supp. 1 (Jun. 1988).

Eyre, et al., "Reducible Crosslinks in Hydroxylysine-Deficient Collagens of a Heritable Disorder of Connective Tissue," Proc. Nat. Acad. Sci. USA 69(9):2594–2598 (Sep. 1972).

Eyre, et al., "Evidence for a previously undetected sequence at the carboxyterminus of the a1 chain of chicken bone collagen," Biochemical and Biophysical Research Communications 48(3):720–726 (1972).

Eyre, et al., "The distribution of crosslinking aldehydes in a1 and a2 chains of chicken bone collagen," Biochimica et Biophysica Acta 278:206–210 (1972).

Eyre, et al., "Evidence for intramolecular crosslinks in chicken bone collagen: the isolation of peptides containing allysine aldol," Biochimica et Biophysica Acta 295:301–307 (1973).

Eyre, et al., "Analysis of a crosslinked peptide from calf bone collagen: evidence that hydroxylysyl glycoside participates in the crosslinks," Biochemical and Biophysical Research Communications 52(2):663–671 (1973).

Eyre, et al., "Isolation of crosslinked peptides from collagen of chicken bone," Biochem J. 135:393–403 (1973).

Eyre, et al., "The hydroxypyridinium crosslinks of skeletal collagens: their measurement, properties and a proposed pathway of formation," Biochemical and Biophysical Research Communications 92(2):403–410 (1980).

Walters, et al., "Collagen Crosslinks in Human Dentin: Increasing Content of Hydroxypyridinium Residues with Age," Calcif. Tissue Int. 35:401–405 (1983).

Wu, et al., "Identification of Hydroxypyridinium Cross-Linking Sites in Type II Collagen of Bovine Articular Cartilage," Biochemistry 23:1850–1857 (1984).

Wu, et al., "Cartilage type IX collagen is cross-linked by hydroxypyridinium residues," Biochemical and Biophysical Research Communications 123(3):1033–1039 (1984).

Eyre, et al., "Collagen type IX: evidence for covalent linkages to type II collagen in cartilage," FEB 220(2):337–341 (1987).

Beardsworth, et al., "Changes with Age in the Urinary Excretion of Lysyl- and Hydroxylysylpyridinoline, Two New Markers of Bone Collagen Turnover," Journal of Bone and Mineral Research 5(7):671–676 (1990).

Eyre, D.R., "Collagen: Molecular Diversity in the Body's Protein Scaffold," Science 207:1315–1322 (1980).

Eyre, D.R., "Collagen Stability Through Covalent Crosslinking," In: Pearson, et al., eds. Advances in Meat Research, vol. 4, Collagen as a Food. New York: Van Nostrand Reinhold, 1987.

Eyre, D.R., "Crosslink maturation in bone collagen," In: Veis, A., ed. The Chemistry and Biology of Mineralized Connective Tissues, Elsevier North Holland, Inc., 1981.

Eyre, D.R., "Collagen cross-linking," In: Akeson, W.H. et al., eds., AAOS: Symposium on Heritable Disorders of Connective Tissue, St. Louis: C.V. Mosby, 1982, pp. 43–58.

Eyre, et al., "Studies on the molecular diversity and cross-linking of cartilage collagen," In: Peyron, J.G., ed. Osteoarthritis: Current Clinical and Fundamental Problems, Paris, France: Ciba–Geigy, 1984, pp. 117–122.

Delmas, Pierre D., "Biochemical Markers of Bone Turnover for the Clinical Assessment of Metabolic Bone Disease," Endocrinology and Metabolism Clinics of North America, 19(1) (Mar. 1990).

Uebelhart, et al. "Urinary excretion of pyridinium crosslinks: a new marker of bone resorption in metabolic bone disease" Bone and Mineral, 8:87–96 (1990).

Uebelhart, et al., "Effect of Menopause and Hormone Replacement Thearpy on the Urinary Excretion of Pyridinium Cross–Links", Journal of Clinical Endocrinology and Metabolism 72(2):367–373 (1991).

Rauterberg, J., et al., "Structural Characterization of N-Terminal Antigenic Determinants in Calf and Human Collagen," Eur. J. Biochem., 27:231–237 (1972).

Rauterberg, J., et al., "The Amino Acid Sequence of the Carboxyterminal Nonhelical Cross Link Region of the α1 Chain of Calf Skin Collagen," FEBS Letters, 21(1):75–79 (1972).

Timpl, R., et al., "Maturation of the Immune Response to Soluble Rat Collagen: Late Appearance of Antibodies Directed to N–Terminal Sites of the α2–Chain," The Journal of Immunology, 108(1):119–125 (1972).

Fig. 1.

DETECTION OF COLLAGEN DEGRADATION IN VIVO

This is a continuation of Ser. No. 08/229,569, filed Apr. 19, 1994 (U.S. Pat. No. 5,472,884), which is a continuation of Ser. No. 07/708,529, filed May 31, 1991 (U.S. Pat. No. 5,320,970), which is a continuation-in-part of Ser. No. 07/614,719, filed Nov. 21, 1990, (U.S. Pat No. 5,300,434), which is a continuation-in-part of Ser. No. 07/444,881, filed Dec. 1, 1989 (U.S. Pat. No. 5,140,103), which is a continuation-in-part of Ser. No. 07/118,234, filed Nov. 6, 1987 (U.S. Pat. No. 4,973,666), the benefits of the filing dates of which are hereby claimed under 35 U.S.C. §120.

This invention was made with government support under grants AR37318 and AR36794 awarded by the National Institutes of Health. The government has certain rights in the invention.

FIELD OF THE INVENTION

The present invention relates to methods for detecting and monitoring collagen degradation in vivo. More specifically, it relates to methods for quantitating certain cross-linked telopeptides produced in vivo upon degradation of collagen and to reagents useful in such methods.

BACKGROUND OF THE INVENTION

Three known classes of collagens have been described to date. The Class I collagens, subdivided into types I, II, III, V, and XI, are known to form fibrils. These collagens are all synthesized as procollagen molecules, made up of N-terminal and C-terminal propeptides, which are attached to the core collagen molecule. After removal of the propeptides, which occurs naturally in vivo during collagen synthesis, the remaining core of the collagen molecule consists largely of a triple-helical domain having terminal telopeptide sequences which are nontriple-helical. These telopeptide sequences have an important function as sites of intermolecular cross-linking of collagen fibrils extracellularly.

The present invention relates to methods of detecting collagen degradation based on assaying for particular cross-linked telopeptides produced in vivo upon collagen degradation. In the past, assays have been developed for monitoring degradation of collagen in vivo by measuring various biochemical markers, some of which have been degradation products of collagen. For example, bone turnover associated with Paget's disease has been monitored by measuring small peptides containing hydroxyproline, which are excreted in the urine following degradation of bone collagen. Russell et al. *Metab. Bone Dis. and Rel. Res.* 4 and 5, 255–262 (1981); and Singer, F. R., et al., *Metabolic Bone Disease*, Vol. II (eds. Avioli, L. V. and Kant, S. M.), 489–575 (1978), Academic Press, New York.

Other researchers have measured the cross-linking compound pyridinoline in urine as an index of collagen degradation in joint disease. See, for background and for example, Wu and Eyre, *Biochemistry*, 23:1850 (1984); Black et al., *Annals of the Rheumatic Diseases*, 48:641–644 (1989); Robins et al.; *Annals of the Rheumatic Diseases*, 45:969–973 (1986); and Seibel et al., *The Journal of Rheumatology*, 16:964 (1989). In contrast to the present invention, some prior researchers have hydrolyzed peptides from body fluids and then looked for the presence of individual hydroxypyridinium residues. None of these researchers has reported measuring a telopeptide containing a cross-link that is naturally produced in vivo upon collagen degradation, as in the present invention.

U.K. Patent application GB 2,205,643 reports that the degradation of type III collagen in the body is quantitatively determined by measuring the concentration of an N-terminal telopeptide from type III collagen in a body fluid.

There are a number of reports indicating that collagen degradation can be measured by quantitating certain procollagen peptides. The present invention involves telopeptides rather than propeptides, the two being distinguished by their location in the collagen molecule and the timing of their cleavage in vivo. See U.S. Pat. No. 4,504,587; U.S. Pat. No. 4,312,853; Pierard et al., *Analytical Biochemistry* 141:127–136 (1984); Niemela, *Clin. Chem.*, 31/8:1301–1304 (1985); and Rohde et al., *European Journal of Clinical Investigation*, 9:451–459 (1979).

U.S. Pat. No. 4,778,768 relates to a method of determining changes occurring in articular cartilage involving quantifying proteoglycan monomer or antigenic fragments thereof in a synovial fluid sample. This patent does not relate to detecting cross-linked telopeptides derived from degraded collagen.

Dodge, *J. Clin. Invest.*, 83:647–661 (1981) discloses methods for analyzing type II collagen degradation utilizing a polyclonal antiserum that specifically reacts with unwound alpha-chains and cyanogen bromide-derived peptides of human and bovine type II collagens. The peptides involved are not cross-linked telopeptides as in the present invention.

Amino acid sequences of human type III collagen, human proα1(II) collagen and the entire preproα1(III) chain of human type III collagen and corresponding cDNA clones have been investigated and determined by several groups of researchers. See Loidl et al., *Nucleic Acids Research* 12:9383–9394 (1984); Sangiorgi et al., *Nucleic Acids Research*, 13:2207–2225 (1985); Baldwin et al., *Biochem. J.*, 262:521–528 (1989); and Ala-Kokko et al., *Biochem. J.*, 260:509–516 (1989). None of these references specifies the structures of particular telopeptide degradation products that could be measured to determine the amount of degraded fibrillar collagen in vivo.

In spite of the above-described background information, there remains a need for effective and simple assays for determining collagen degradation in vivo. Such assays could be used to detect and monitor disease states in humans, such as osteoarthritis (type II collagen degradation), and various inflammatory disorders, such as vasculitis syndrome (type III collagen degradation).

Assays for type I collagen degradation, described in a parent application, U.S. Ser. No. 118,234, can be utilized to detect and assess the rate of bone resorption in vivo. Detection of the rate of bone resorption may be a factor of interest in monitoring and detecting diseases such as osteoporosis. Osteoporosis is the most common bone disease in man. Primary osteoporosis, with increased susceptibility to fractures, results from a progressive net loss of skeletal bone mass. It is estimated to affect 15–20 million individuals in the United States. Its basis is an age-dependent imbalance in bone remodeling, i.e., in the rates of synthesis and degradation of bone tissue.

About 1.2 million osteoporosis-related fractures occur in the elderly each year including about 538,000 compression fractures of the spine, about 227,000 hip fractures and a substantial number of early fractured peripheral bones. Twelve to 20% of the hip fractures are fatal because they cause severe trauma and bleeding, and half of the surviving patients require nursing home care. Total costs from osteoporosis-related injuries now amount to at least $7 billion annually (Barnes, O. M., *Science*, 236:914 (1987)).

Osteoporosis is most common in postmenopausal women who, on average, lose 15% of their bone mass in the 10 years after menopause. This disease also occurs in men as they get older and in young amenorrheic women athletes. Despite the major, and growing, social and economic consequences of osteoporosis, no method is available for measuring bone resorption rates in patients or normal subjects. A major difficulty in monitoring the disease is the lack of a specific assay for measuring bone resorption rates.

Methods for assessing bone mass often rely on measuring whole-body calcium by neutron activation analysis or mineral mass in a given bone by photon absorption techniques. These measurements can give only long-term impressions of whether bone mass is decreasing. Measuring calcium balances by comparing intake with output is tedious, unreliable and can only indirectly appraise whether bone mineral is being lost over the long term. Other methods currently available for assessing decreased bone mass and altered bone metabolism include quantitative scanning radiometry at selected bone locations (wrist, calcaneus, etc.) and histomorphometry of iliac crest biopsies. The former provides a crude measure of the bone mineral content at a specific site in a single bone. Histomorphometry gives a semiquantitative assessment of the balance between newly deposited bone seams and resorbing surfaces.

A urinary assay for the whole-body output of degraded bone in 24 hours would be much more useful. Mineral studies (e.g., calcium balance) cannot do this reliably or easily. Since bone resorption involves degradation of the mineral and the organic matrix, a specific biochemical marker for newly degraded bone products in body fluids would be the ideal index. Several potential organic indices have been tested. For example, hydroxyproline, an amino acid largely restricted to collagen, and the principal structural protein in bone and all other connective tissues, is excreted in urine. Its excretion rate is known to be increased in certain conditions, notably Paget's disease, a metabolic bone disorder in which bone turnover is greatly increased, as pointed out above. For this reason, urinary hydroxyproline has been used extensively as an amino acid marker for collagen degradation. Singer, F. R., et al. (1978), cited hereinabove.

U.S. Pat. No. 3,600,132 discloses a process for determination of hydroxyproline in body fluids such as serum, urine, lumbar fluid and other intercellular fluids in order to monitor deviations in collagen metabolism. In particular, this inventor notes that in pathologic conditions such as Paget's disease, Marfan's syndrome, osteogenesis imperfecta, neoplastic growth in collagen tissues and in various forms of dwarfism, increased collagen anabolism or catabolism as measured by hydroxyproline content in biological fluids can be determined. This inventor measures hydroxyproline by oxidizing it to a pyrrole compound with hydrogen peroxide and N-chloro-p-toluenesulphonamide followed by colorimetric determination in p-dimethyl-amino-benzaldehyde.

In the case of Paget's disease, the increased urinary hydroxyproline probably comes largely from bone degradation; hydroxyproline, however, generally cannot be used as a specific index. Much of the hydroxyproline in urine may come from new collagen synthesis (considerable amounts of the newly made protein are degraded and excreted without ever becoming incorporated into tissue fabric), and from turnover of certain blood proteins as well as other proteins that contain hydroxyproline. Furthermore, about 80% of the free hydroxyproline derived from protein degradation is metabolized in the liver and never appears in the urine. Kiviriko, K. I. *Int. Rev. Connect. Tissue Res.* 5:93 (1970), and Weiss, P. H. and Klein, L., *J. Clin. Invest.* 48:1 (1969).

Hydroxylysine and its glycoside derivatives, both peculiar to collagenous protein, have been considered to be more accurate than hydroxyproline as markers of collagen degradation. However, for the same reasons described above for hydroxyproline, hydroxylysine and its glycosides are probably equally non-specific markers of bone resorption. Krane, S. M. and Simon, L. S. *Develop. Biochem.*, 22:185 (1981).

In addition to amino acids unique to collagen, various non-collagenous proteins of bone matrix such as osteocalcin, or their breakdown products, have formed the basis of immunoassays aimed at measuring bone metabolism. Price, P. A. et al. *J. Clin. Invest.*, 66:878 (1980), and Gundberg, C. M. et al., *Meth. Enzymol.*, 107:516 (1984). However, it is now clear that bone-derived non-collagenous proteins, though potentially a useful index of bone metabolic activity are unlikely, on their own, to provide quantitative measures of bone resorption. The concentration in serum of osteocalcin, for example, fluctuates quite widely both normally and in metabolic bone disease. Its concentration is elevated in states of high skeletal turnover but it is unclear whether this results from increased synthesis or degradation of bone. Krane, S. M., et al., *Develop. Biochem.*, 22:185 (1981), Price, P. A. et al., *J. Clin. Invest.*, 66:878 (1980); and Gundberg, C. M. et al., *Meth. Enzymol.*, 107:516 (1984).

Collagen Cross-Linking

The polymers of most genetic types of vertebrate collagen require the formation of aldehyde-mediated cross-links for normal function. Collagen aldehydes are derived from a few specific lysine or hydroxylysine side-chains by the action of lysyl oxidase. Various di-, tri- and tetrafunctionl cross-linking amino acids are formed by the spontaneous intra- and intermolecular reactions of these aldehydes within the newly formed collagen polymers; the type of cross-linking residue varies specifically with tissue type (see Eyre, D. R. et al., *Ann. Rev. Biochem.*, 53:717–748 (1984)).

Two basic pathways of cross-linking can be differentiated for the banded (67 nm repeat) fibrillar collagens, one based on lysine aldehydes, the other on hydroxylysine aldehydes. The lysine aldehyde pathway dominates in adult skin, cornea, sclera, and rat tail tendon and also frequently occurs in other soft connective tissues. The hydroxylysine aldehyde pathway dominates in bone, cartilage, ligament, most tendons and most internal connective tissues of the body, Eyre, D. R. et al. (1984) vida supra. The operating pathway is governed by whether lysine residues are hydroxylated in the telopeptide sites where aldehyde residues will later be formed by lysyl oxidase (Barnes, M. J. et al., *Biochem. J.*, 139:461 (1974)).

The chemical structure(s) of the mature cross-linking amino acids on the lysine aldehyde pathway are unknown, but hydroxypyridinium residues have been identified as mature products on the hydroxylysine aldehyde route. On both pathways and in most tissues the intermediate, borohydride-reducible cross-linking residues disappear as the newly formed collagen matures, suggesting that they are relatively short-lived intermediates (Bailey, A. J. et al., *FEBS Lett.*, 16:86 (1971)). Exceptions are bone and dentin, where the reducible residues persist in appreciable concentration throughout life, in part apparently because the rapid mineralization of the newly made collagen fibrils inhibits further spontaneous cross-linking interactions (Eyre, D. R., In: *The Chemistry and Biology of Mineralized Connective Tissues*, (Veis, A. ed.) pp. 51–55 (1981), Elsevier, New York, and Walters, C. et al., *Calc. Tiss. Intl.*, 35:401–405 (1983)).

Two chemical forms of 3-hydroxypyridinium cross-link have been identified (Formula I and II). Both compounds are naturally fluorescent, with the same characteristic excitation and emission spectra (Fujimoto, D. et al. *Biochem. Biophys. Res. Commun.*, 76:1124 (1977), and Eyre, D. R., *Develop. Biochem.*, 22:50 1981)). These amino acids can be resolved and assayed directly in tissue hydrolysates with good sensitivity using reverse phase HPLC and fluorescence detection. Eyre, D. R. et al., *Analyte. Biochem.*, 137:380–388 (1984). It should be noted that the present invention involves quantitating particular peptides rather than amino acids.

In growing animals, it has been reported that these mature cross-links may be concentrated more in an unmineralized fraction of bone collagen than in the mineralized collagen (Banes, A. J., et al., *Biochem. Biophys. Res. Commun.*, 113:1975 (1983). However, other studies on young bovine or adult human bone do not support this concept, Eyre, D. R., In: *The Chemistry and Biology of Mineralized Tissues* (Butler, W. T. ed.) p. 105 (1985), Ebsco Media Inc., Birmingham, Ala.

The presence of collagen hydroxypyridinium cross-links in human urine was first reported by Gunja-Smith and Boucek (Gunja-Smith, Z. and Boucek, R. J., *Biochem J.*, 197:759–762 (1981)) using lengthy isolation procedures for peptides and conventional amino acid analysis. At that time, they were aware only of the HP form of the cross-link. Robins (Robins, S. P., *Biochem J.*, 297:617–620 (1982) has reported an enzyme-linked immunoassay to measure HP in urine, having raised polyclonal antibodies to the free amino acid conjugated to bovine serum albumin. This assay is intended to provide an index for monitoring increased joint destruction that occurs with arthritic diseases and is based, according to Robins, on the finding that pyridinoline is much more prevalent in cartilage than in bone collagen.

In more recent work involving enzyme-linked immunoassay, Robins reports that lysyl pyridinoline is unreactive toward antiserum to pyridinoline covalently linked to bovine serum albumin (Robins et al., *Ann. Rheum. Diseases*, 45:969–973 (1986)). Robins' urinary index for cartilage destruction is based on the discovery that hydroxylysyl pyridinoline, derived primarily from cartilage, is found in urine at concentrations proportional to the rate of joint cartilage resorption (i.e., degradation). In principle, this index could be used to measure whole body cartilage loss; however, no information on bone resorption would be available.

A need therefore exists for a method that allows the measurement of whole-body bone resorption rates in humans. The most useful such method would be one that could be applied to body fluids, especially urine. The method should be sensitive, i.e., quantifiable down to 1 picomole and rapidly measure 24-hour bone resorption rates so that the progress of various therapies (e.g., estrogen) can be assessed.

Prior U.S. Ser. Nos. 614,719, 444,881 and 118,234, which are hereby incorporated by reference herein, disclosed particular peptides, methods of assaying for collagen degradation based on detecting these peptides, and kits useful for practicing the methods. Additionally, U.S. Ser. No. 614,719 disclosed a particular monoclonal antibody MAb-1H11 that is capable of binding to a peptide having the following structure:

FORMULA III where is hydroxylysyl pyridinoline (HP) or lysyl pyridinoline (LP), and Gln is glutamine or pyrrolidone carboxylic acid, and other peptides that contain the same binding epitope. The present invention is based on these prior discoveries, but provides additional previously undisclosed elements thereof.

SUMMARY OF THE INVENTION

The present invention provides certain novel peptides derived from type I collagen that are produced in vivo and that may be found in body fluids. These peptides are recognized and bound by the antibody MAb-1H11. Structures of the peptides have been determined and/or verified by electrospray mass spectrometry (using a SCIEX instrument). The structures of the peptides isolated from urine using MAb-1H11 are reported hereinbelow in the description of FIG. 1, and include the type I collagen peptide having the formula reported previously in U.S. Pat. No. 4,973,666, as well as some relatively minor variants thereof. Additionally, a previously unknown peptide was discovered in urine using this affinity chromatography technique. This peptide, corresponding to peak D in FIG. 1, and having the structure provided in the description of FIG. 1 below, is a peptide composed of two segments of α(2) chains of collagen. The present invention relates to this dimeric peptide, methods of analyzing collagen degradation, which is correlated to the rate of bone resorption, based on quantitating the peptide, and kits for such quantitation.

BRIEF DESCRIPTION OF THE DRAWINGS

wherein J represents pyroglutamic acid or glutamine and the parentheses indicate that an amino acid may or may not be present.

DETAILED DESCRIPTION OF THE PREFERRED EMBODIMENTS

Cross-Linked Peptides

The present invention relates to cross-linked peptides isolatable from urine that are derived from type I collagen and are released when bone is resorbed in vivo. These peptides occur naturally in body fluids, such as urine, and may be isolated by standard purification protocols. The purified peptides may be used, for example, as antigens to produce immunological binding partners thereto. A preferred purification protocol employs the antibody MAb-1H11. The hybridoma (1H11) that produces this preferred monoclonal antibody has been deposited at the American Type Culture Collection (ATCC), 12301 Parklawn Drive, Rockville, Md. 20852, under accession No. 10611. Purification of these peptides by affinity chromatography using monoclonal antibodies produced by 1H11 results in highly purified bone-type I collagen cross-linked N-telopeptides, as shown in FIG. 1.

Figure 1:
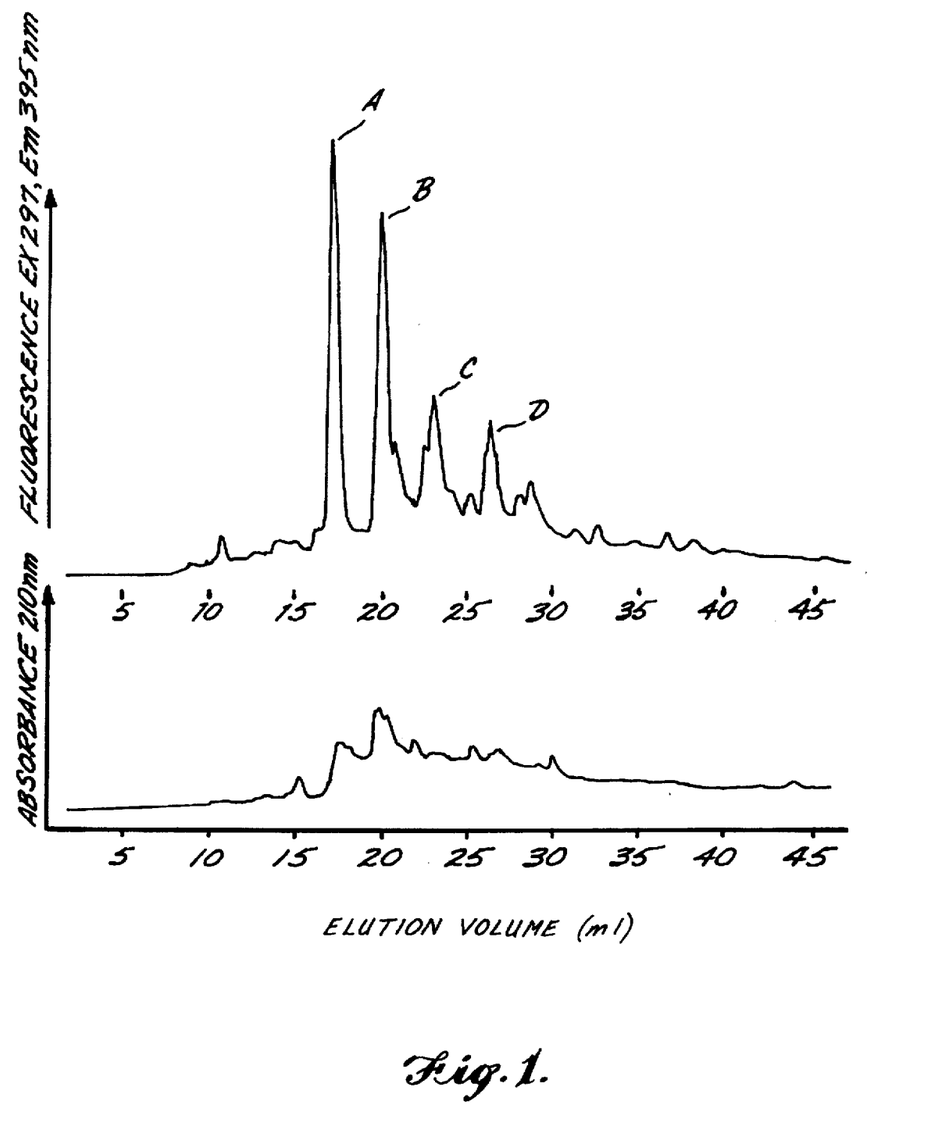
FIG. 1 depicts an elution profile of peptides isolated by affinity chromatography from human urine. The structures of the peptides, as determined by mass spectrometry, are as follows.

A particularly interesting peptide isolated in this manner corresponds to peak D in FIG. 1, which has the following structure:

wherein J is pyroglutamic acid or glutamine, (Leu) means optional leucines (i.e., either leucine may be present, both leucines may be present, or neither leucine may be present), and the cross-linking amino acid HP or LP is represented by the connected K residues. Although the above structure covers several peptides, for convenience, the following discussion refers to a single peptide.

This structure is surprising in that it implies that it is derived from three entirely separate collagen molecules that are cross-linked together. There has been some controversy in the scientific literature as to whether cross-linking of collagen molecules occurs intramolecularly or intermolecularly. The structure of the above dimeric peptide supports the latter view.

In more practical terms, the above-described peptide may be used in an assay for the rate of bone resorption. Under these circumstances, the procedures, techniques, kits, etc., disclosed in the prior related applications, which have been incorporated by reference above, may be employed analogously with this peptide.

A preferred method of quantitating this peptide (and its equivalents) employs an immunological binding partner thereto. The peptide is utilized as an antigen, either alone or conjugated to a carrier molecule to produce antibodies, which may be polyclonal or monoclonal, or binding fragments thereof. Binding fragments may also be produced recombinantly, if desired. Monoclonal antibodies are preferred. An especially preferred monoclonal antibody is that produced by 1H11, described herein. The amount of this peptide in a body fluid may be correlated directly to the absolute rate of bone resorption, or the level of this peptide may be correlated to other type I collagen peptides that occur in greater quantities, which in turn may be correlated to the absolute rate of bone resorption. A kit containing reagents, etc., for quantitating this peptide is also contemplated in accordance with the present invention. These kits would typically include containers of appropriate reagents, such as immunological binding partners to the above-described peptide, suitable controls, competitive binding reagents, and the like. Any other standard method of peptide quantitation may also be employed for these purposes. Kits for carrying out such methods are also contemplated.

By analogy to the disclosure incorporated herein from prior U.S. Ser. No. 614,719, the pyridinoline ring contained in the above-described peptide may be open or closed. An assay based on quantitating either form or both forms of the peptide, and kits for carrying out the assay, are also contemplated.

In addition to the dimeric peptide described above, additional peptides corresponding to Formula III in U.S. Ser. No. 118,234, now issued as U.S. Pat. No. 4,973,666, are also isolatable from urine. These peptides illustrate the fact that a small number of amino acids (e.g., 1–3) may be attached to the N or C termini of the peptides in body fluids. For example, the peptides of Formula III may have a Tyr residue attached to the N-terminal of the α1 (I) chain. Also, the the peptide corresponding to peak A in FIG. 1 is an equivalent of the peptides contained in peaks B and C. Analogously, the peptide falling within peak D is also expected to have equivalent peptides in which one or a small number of amino acids are combined with the N or C termini thereof. These amino acids will typically correspond to the amino acids normally found in type I collagen molecules in vivo. The language "consisting essentially of" includes such peptide equivalents.

A preferred method of isolating the peptides described above, and schematically shown in FIG. 1, will now be described:

Affinity-column Purification of Cross-linked N-telopeptides from Human Bone Collagen 1. Preparation of Column Monoclonal antibody (MAb) 1H11 was coupled to CNBr-activated Sepharose® (Pharmacia) by conventional methods (manufacturer's protocol). Mouse ascites fluid (3 ml) containing MAb 1H11 was adsorbed on a Protein G-Sepharose® affinity column diluted (1:1 v/v) in 0.15M NaCl, 0.025M Tris-HCl (TBS), pH 7.5. After washing in the same buffer, IgG was eluted by 0.1M glycine-HCl, pH 2.5, dialysed against the coupling buffer and coupled to activated Sepharose®.

2. Binding and Elution of Urinary Peptides

Urine (17-year adolescent, male) was diluted with TBS, pH 7.5 (1:1 v/v) and eluted dropwise at 25° C. through the 1H11 affinity column (5 ml bed volume). After washing with TBS, bound peptides were eluted with 50% saturated ammonium sulfate containing 1% (v/v) trifluoroacetic acid (TFA). The eluted peptides were passed through a pre-conditioned C18-Sep-Pak (Waters), bound peptides were eluted with 50% (v/v) acetonitrile and dried. Individual peptides were resolved by reverse-phase HPLC (C8, RP-300 Brownlee) using an acetonitrile:n-propanol (3:1 v/v) gradient in aqueous 0.1% (v/v) TFA. Highly purified bone type I collagen cross-linked N-telopeptides were recovered (see FIG. 1).

While the invention has been described in conjunction with preferred embodiments, one of ordinary skill after reading the foregoing specification will be able to effect various changes, substitutions of equivalents, and alterations to the subject matter set forth herein. Hence, the invention can be practiced in ways other than those specifically described herein. It is therefore intended that the protection granted by Letters Patent hereon be limited only by the appended claims and equivalents thereof.

The embodiments of the invention in which an exclusive property or privilege is claimed are defined as follows:

1. In a method of analyzing a body fluid sample for the presence or concentration of an analyte indicative of a physiological condition, comprising the steps of contacting the body fluid sample with an immunological binding partner which binds to the analyte, detecting binding of the immunological binding partner in the body fluid sample, and correlating any detected binding to the physiological condition, the improvement comprising contacting the body fluid sample with an immunological binding partner which binds to both and wherein is hydroxylysyl pyridinoline or lysyl pyridinoline, J is pyroglutamic acid or glutamine, and (Leu) are optional leucine residues, and correlating any detected binding to degradation of type I collagen in vivo.

2. An immunological binding partner which binds to both and wherein is hydroxylysyl pyridinoline or lysyl pyridinoline, J is pyroglutamic acid or glutamine, and (Leu) are optional leucine residues.

3. The immunological binding partner of claim 2, wherein comprises a pyridinoline ring that may be open or closed.

* * * * *

UNITED STATES PATENT AND TRADEMARK OFFICE
CERTIFICATE OF CORRECTION

PATENT NO. : 5,688,652  Page 1 of 5
DATED : November 18, 1997
INVENTOR(S) : D.R. Eyre It is certified that error appears in the above-indentified patent and that said Letters Patent is hereby corrected as shown below:

| COLUMN | LINE | |
|---|---|---|
| [63] Pg. 1, col. 1 | Related U.S. App. Data line 5 of text | "Ser. No. 448,881," should read --Ser. No. 444,881,-- |
| [56] Pg. 2, col. 1 | Refs. Cited (Other Publs., Item 10) | "7:1251-1256" should read --7:1251-1258-- |
| [56] Pg. 2, col. 1 | Refs. Cited (Other Publs., Item 18) | "deoxpyridinoline" should read --deoxypyridinoline-- |
| [56] Pg. 2, col. 2 | Refs. Cited (Other Publs., Item 27) | After "28:221-231" insert --,-- |
| [56] Pg. 2, col. 2 | Refs. Cited (Other Publs., Item 28) | After "*Types*" delete "," |
| [56] Pg. 2, col. 2 | Refs. Cited (Other Publs., Item 29) | After "97:196-212" insert --,-- |
| [56] Pg. 2, col. 2 | Refs. Cited (Other Publs., Item 30) | After "98:128-134" insert --,-- |

UNITED STATES PATENT AND TRADEMARK OFFICE
CERTIFICATE OF CORRECTION

PATENT NO. : 5,688,652            Page 2 of 5
DATED : November 18, 1997
INVENTOR(S) : D.R. Eyre It is certified that error appears in the above-indentified patent and that said Letters Patent is hereby corrected as shown below:

| COLUMN | LINE | |
|---|---|---|
| [56] Pg. 2, col. 2 | Refs. Cited (Other Publs., Item 31) | After "27:3560-3567" insert --,-- |
| [56] Pg. 2, col. 2 | Refs. Cited (Other Publs., Item 33) | After "20:996-1006" insert --,-- |
| [56] Pg. 3, col. 2 | Refs. Cited (Other Publs., Item 76) | After "Kang" insert --,-- |
| [56] Pg. 4, col. 2 | Refs. Cited (Other Publs., Item 107) | "Thearpy" should read --Therapy-- |
| 1 | 49-50 | After "Russell et al." insert --,-- |
| 1 | 52 | "Kant," should read --Kane,-- |
| 1 | 59 | After "Robins et al." delete ";" and insert therefor --,-- |
| 3 | 66 | After "Kiviriko, K.I." insert --,-- |
| 4 | 2 | "protein," should read --proteins,-- |
| 4 | 7 | After "Simon, L.S." insert --,-- |

UNITED STATES PATENT AND TRADEMARK OFFICE
CERTIFICATE OF CORRECTION

PATENT NO. : 5,688,652  Page 3 of 5
DATED : November 18, 1997
INVENTOR(S) : D.R. Eyre It is certified that error appears in the above-indentified patent and that said Letters Patent is hereby corrected as shown below:

| COLUMN | LINE | |
|---|---|---|
| 4 | 12 | After "Price, P.A. et al." insert --,-- |
| 4 | 31 | "tetrafunctionl" should read --tetrafunctional-- |
| 5 | 2 | After "Fujimoto, D. et al." insert --,-- |
| 5 | 4 | Before "1981))." insert --(-- |
| 5 | 58 | "297:617-620" should read --207:617-620-- |
| 7 (FORMULA VIII) | 25-27 | " |

$$\begin{array}{c} \text{J-Tyr—Asp—Glu-K-Gly—Val—Gly—(Leu)} \\ | \\ \text{J-Tyr—Asp—Gly-K-Gly—Val—Gly—(Leu)} \\ | \\ \text{K} \end{array}$$
"

should read

--
$$\begin{array}{c} \text{J-Tyr—Asp—Gly-K-Gly—Val—Gly—(Leu)} \\ | \\ \text{J-Tyr—Asp—Gly-K-Gly—Val—Gly—(Leu)} \\ | \\ \text{K} \end{array}$$
--

UNITED STATES PATENT AND TRADEMARK OFFICE
CERTIFICATE OF CORRECTION

PATENT NO. : 5,688,652
DATED : November 18, 1997
INVENTOR(S) : D.R. Eyre

It is certified that error appears in the above-indentified patent and that said Letters Patent is hereby corrected as shown below:

| COLUMN | LINE | |
|---|---|---|
| 7 | 47 | "No. 10611." should read --No. HB 10611.-- |
| 8 | 49-50 | "the the peptide" should read --the peptide-- |
| 10 (Claim 1) | 2-5 | " |

$$\begin{array}{c} \text{J–Tyr–Asp–Glu–K–Gly–Val–Gly–(Leu)} \\ | \\ \text{J–Tyr–Asp–Gly–K–Gly–Val–Gly–(Leu)} \\ | \\ \text{K} \end{array}\quad"$$

should read $$--\begin{array}{c} \text{J–Tyr–Asp–Gly–K–Gly–Val–Gly–(Leu)} \\ | \\ \text{J–Tyr–Asp–Gly–K–Gly–Val–Gly–(Leu)} \\ | \\ \text{K} \end{array}\quad--$$

UNITED STATES PATENT AND TRADEMARK OFFICE
CERTIFICATE OF CORRECTION

PATENT NO. : 5,688,652

DATED : November 18, 1997

INVENTOR(S) : D.R. Eyre

It is certified that error appears in the above-indentified patent and that said Letters Patent is hereby corrected as shown below:

COLUMN      LINE

10      25-27      "
(Claim 2)

$$\begin{array}{c} \text{J-Tyr-Asp-Glu-K-Gly-Val-Gly-(Leu)} \\ | \\ \text{J-Tyr-Asp-Gly-K-Gly-Val-Gly-(Leu)} \\ | \\ \text{K} \end{array}$$

"

should read

--

$$\begin{array}{c} \text{J-Tyr-Asp-Gly-K-Gly-Val-Gly-(Leu)} \\ | \\ \text{J-Tyr-Asp-Gly-K-Gly-Val-Gly-(Leu)} \\ | \\ \text{K} \end{array}$$

--

Signed and Sealed this

Fourteenth Day of July, 1998

*Attest:*

BRUCE LEHMAN

*Attesting Officer*      *Commissioner of Patents and Trademarks*